(12) United States Patent
Douglas

(10) Patent No.: US 9,227,046 B1
(45) Date of Patent: Jan. 5, 2016

(54) INTRAVENOUS LINE COUPLING APPARATUS

(76) Inventor: Calvin Douglas, Fair Oaks, CA (US)

( * ) Notice: Subject to any disclaimer, the term of this patent is extended or adjusted under 35 U.S.C. 154(b) by 394 days.

(21) Appl. No.: 13/472,264

(22) Filed: May 15, 2012

(51) Int. Cl.
*A61M 39/10* (2006.01)
*A61M 25/16* (2006.01)

(52) U.S. Cl.
CPC ....... *A61M 39/10* (2013.01); *A61M 2039/1077* (2013.01)

(58) Field of Classification Search
CPC ... A61M 39/00; A61M 39/10; A61M 39/105; A61M 2039/1077; A61M 2039/1083; A61M 2039/1088; A61M 25/0054; A61M 25/007; A61M 25/0068; A61M 25/0029; A61M 25/0009; A61M 39/1011; A61M 39/12; A61M 2039/1027; A61M 25/0014
USPC ............ 604/80, 25, 262, 523, 533, 535, 538, 604/534
See application file for complete search history.

(56) References Cited

U.S. PATENT DOCUMENTS

| | | | | |
|---|---|---|---|---|
| 4,795,429 A | * | 1/1989 | Feldstein | ........................ 604/80 |
| 5,207,643 A | * | 5/1993 | Davis | .............................. 604/80 |
| 5,658,265 A | * | 8/1997 | Hiruta | ..................... F16L 39/06 604/174 |
| 6,315,759 B1 | | 11/2001 | Peterson | |
| 6,317,623 B1 | * | 11/2001 | Griffiths et al. | ............... 600/431 |
| 6,328,730 B1 | * | 12/2001 | Harkrider, Jr. | ..... A61B 17/3421 600/130 |
| 6,913,601 B2 | * | 7/2005 | St. Goar et al. | ............... 604/509 |
| 2004/0077998 A1 | | 4/2004 | Morris | |

FOREIGN PATENT DOCUMENTS

GB    002233563    *    1/1991

* cited by examiner

*Primary Examiner* — Kami A Bosworth
*Assistant Examiner* — Bradley G Thomas, Jr.
(74) *Attorney, Agent, or Firm* — John P. O'Banion

(57) ABSTRACT

An intravenous (IV) coupling apparatus is disclosed for fluid delivery to a patient. The coupling includes a tube having an input end and an output end, wherein the input end includes a plurality of input connections configured to releasably couple to one or more input lines in communication with one or more fluid sources, and the output end includes a plurality of output connections configured to releasably couple to one or more output lines configured to deliver fluid to the patient. The coupling includes a plurality of lumens disposed within the tube substantially along the length of the tube, wherein each lumen couples one of the input connectors in fluid communication with a corresponding output connector such that an input line is in fluid communication with a corresponding output line when the input line and output line are connected to a corresponding input connector and output connector.

9 Claims, 5 Drawing Sheets

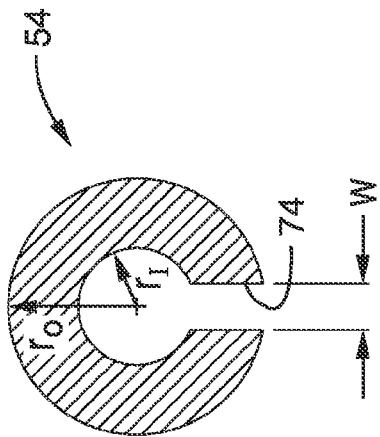
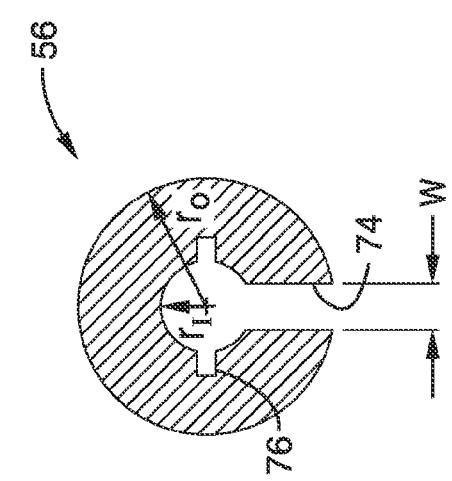
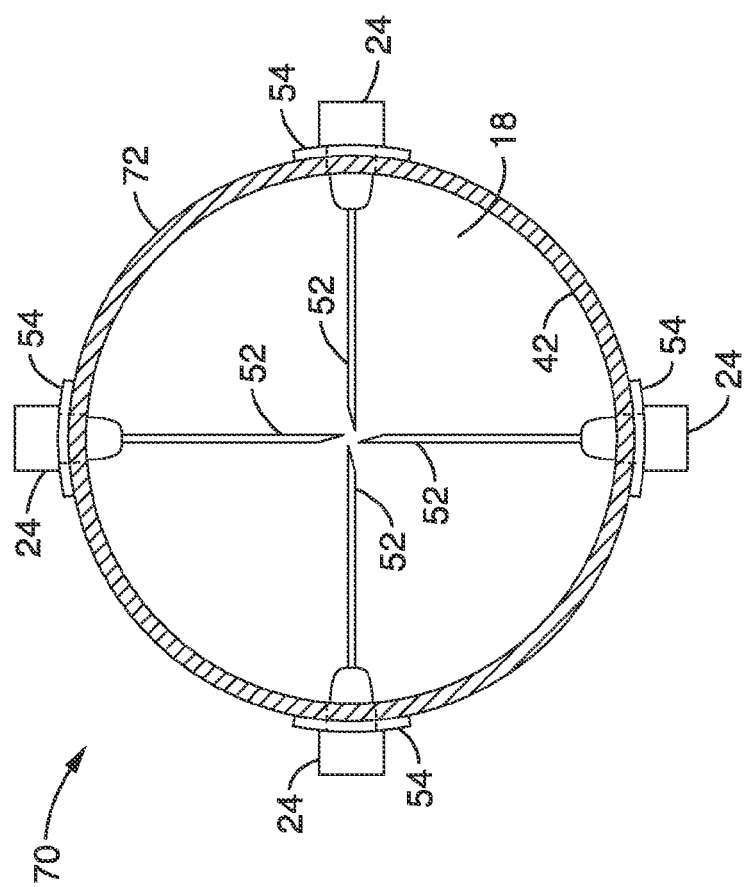

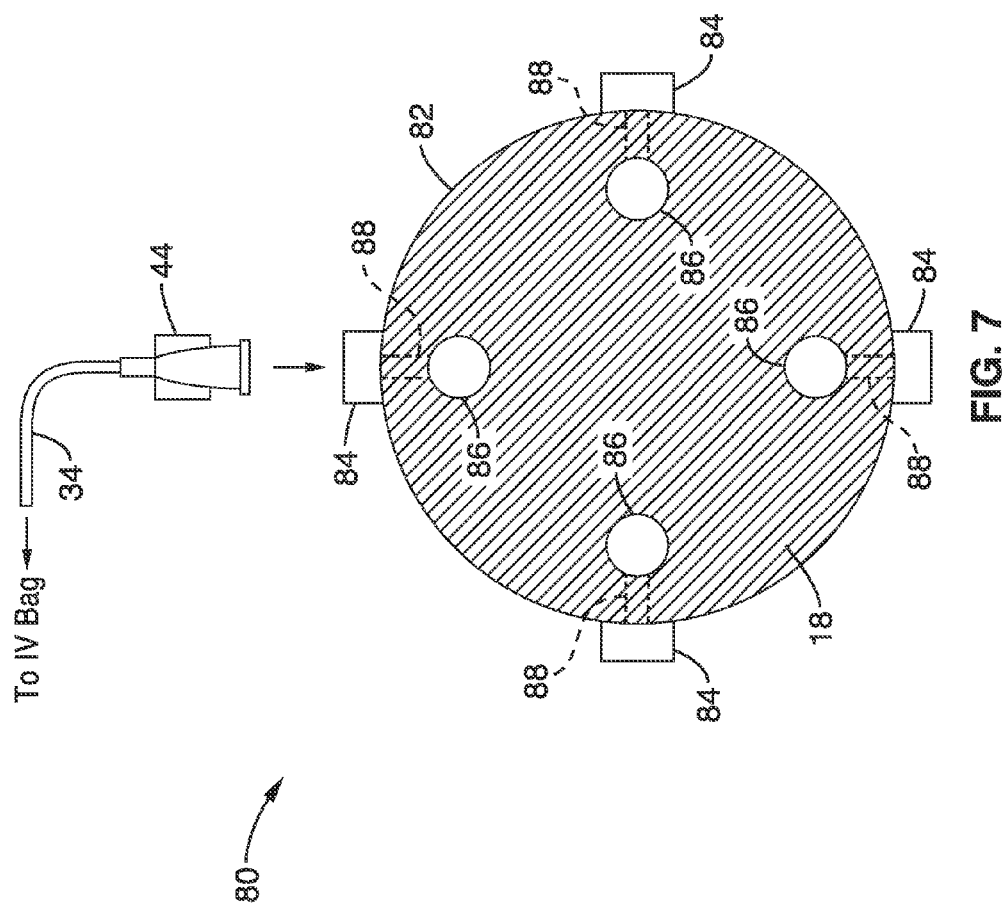

US 9,227,046 B1

INTRAVENOUS LINE COUPLING APPARATUS

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to fluid delivery lines, and more particularly to fluid delivery lines for hospitals.

2. Description of Related Art

During certain medical procedures and hospitalization, patients are often connected to a number of fluid sources for the purposes of, providing medications, hydration and other fluids. The fluid sources are generally coupled to the patient via lines such as catheters, intravenous (IV) and fluid lines. Many of these lines and tubes are connected to the patient during transport, and have a tendency to become entangled and confused. In addition, there is a risk that the lines will be disturbed or even disconnected if caught on a projection while the patient is being transported. A mass of entangled lines and tubes also gives family members and loved ones anxious feelings when seeing a patient treated in this manner.

Management of fluid delivery lines has also become a costly exercise for health care professionals. It may often take a nurse twenty to thirty minutes to reconnect IV lines after a patient is sent for a procedure.

Attempts to solve this problem have generally comprised a sleeve or cover that is wrapped around a segment of the IV lines, such as those devices described in U.S. Pat. No. 6,315,759, and U.S. Patent Serial No. 2004/0077998. However, both of these devices still allow the IV lines to become tangled within the covering. Because the IV lines are not anchored in within the covering, they are prone to tangling and inadvertent cessation of fluid flow to the patient.

Accordingly, an object of the present invention is an IV line management system that allows for quick coupling and decoupling of lines to the patient and means for maintaining the continuity of the lines without tangling. At least some of these objectives will be met in the description below.

BRIEF SUMMARY OF THE INVENTION

An aspect of the invention is an intravenous (IV) coupling apparatus for fluid delivery to a patient. The coupling includes a tube (e.g. ventilator tubing) having an input end, an output end, such that the input end includes a plurality of input connections configured to releasably couple to one or more input lines in communication with one or more fluid sources, and the output end includes a plurality of output connections configured to releasably couple to one or more output lines configured to deliver fluid to the patient. The coupling includes a plurality of lumens (e.g. IV lines) disposed within the tube substantially along the length of the tube, wherein each lumen couples one of the input connectors in fluid communication with a corresponding output connector such that an input line is in fluid communication with a corresponding output line when the input line and output line are connected to a corresponding input connector and output connector.

The fluid delivery line coupling device of the present invention is configured to provide a secure and shielded protective tubing for fluid delivery (e.g. IV) lines such that the lines are free from tangling within each other or other objects or people in their vicinity. The coupling allows for quick coupling and/ or recoupling of IV lines to IV bags and a patient (e.g. within 5 minutes). The lines are substantially shielded from external debris (e.g. infection carrying dust or particulates), resulting in improved safety, and time and money savings for hospitals.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 4 is a side view of a fluid delivery line coupling device having a radial input line configuration.

FIG. 5 is a plan view of a retainer for coupling IV extension lines to carrier tubing in accordance with the present invention.

FIG. 6 is a plan view of an alternative retainer for coupling IV extension lines to carrier tubing in accordance with the present invention.

FIG. 7 shows a cross-sectional view of an integrated fluid delivery line coupling device in accordance with the present invention.

DETAILED DESCRIPTION OF THE INVENTION

Figure 1:
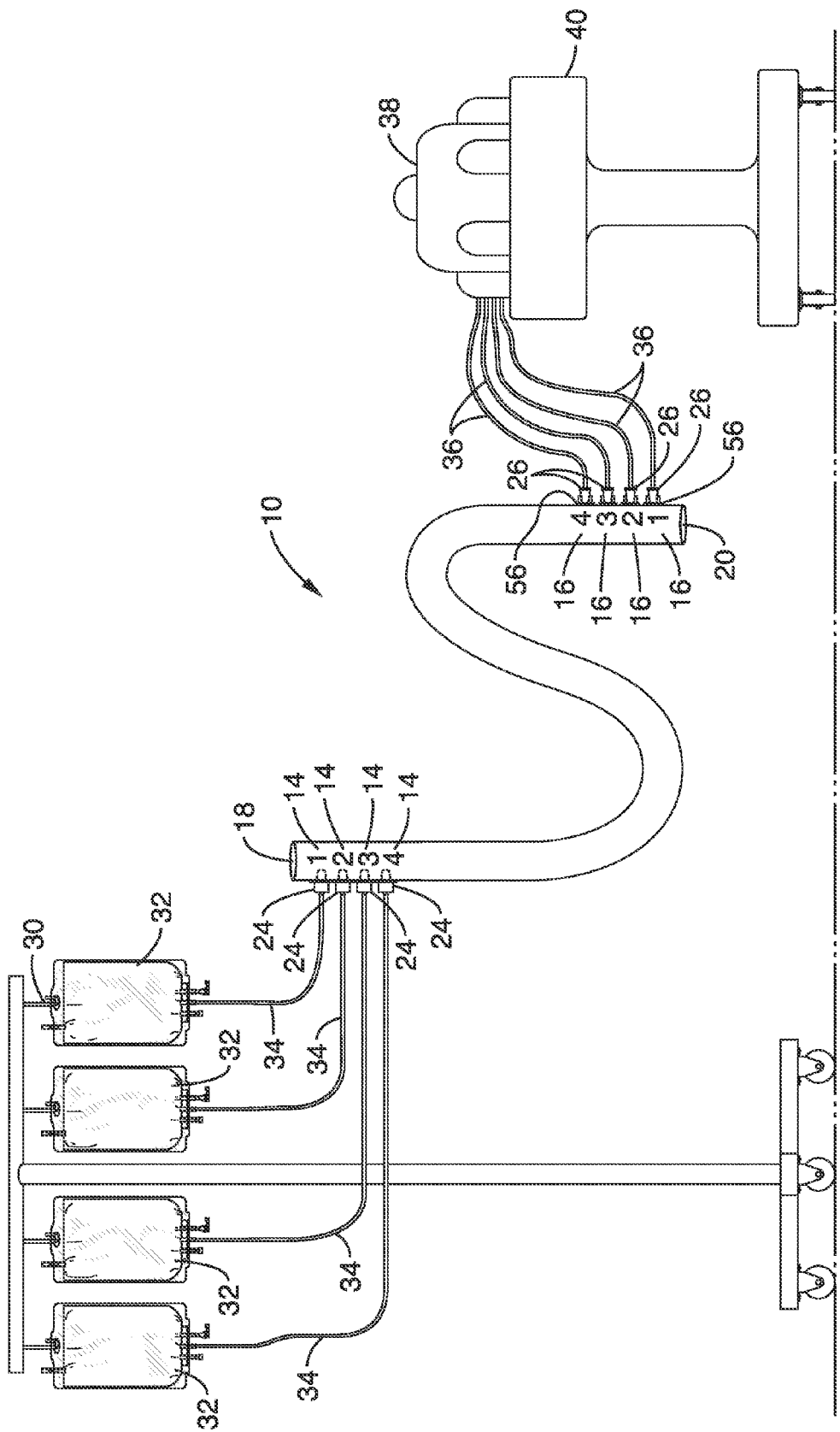
FIG. 1 illustrates a fluid delivery line coupling device coupled to a plurality of fluid sources and a patient in a hospital setting in accordance with the present invention.

FIG. 1 illustrates a fluid delivery line coupling device 10 in accordance with the present invention coupled to a plurality of fluid sources 32 and a patient 38. The embodiments shown in FIGS. 1 through 7 are predominantly shown with couplings for intravenous (IV) lines; however it is appreciated that the coupling devices shown in FIGS. 1-7 may be used with any type of fluid delivery line or combination of fluid delivery line types.

Coupling device 10 comprises a carrier tube 12 (e.g. ventilator tubing or the like) having an input end 18 with a plurality of input connections 24 for coupling to input IV lines 34. The input IV lines 34 interface at their opposite ends with respective fluid sources (e.g. IV bags 32) that are hanging on IV pole 30.

The carrier tube 12 has an output end 20 with a plurality of output connections 26 for coupling to IV lines 36 that output fluid from tube 12 for input to the patient 38.

The carrier tube 12 is generally sized to have a length (e.g. 6 to 8 feet) corresponding to the distance between the IV pole 30 and the patient 38 on bed 40. The diameter of the carrier tube 12 may also vary, depending on the number of connections. The embodiments shown in FIGS. 1-4 are shown with four connections (e.g. four inputs 24 and four outputs 26). However, it is appreciated that any number of connections may be provided, (e.g. six, eight, ten, etc.).

Each of the input connections 24 and output connections 26 comprises a dedicated, independent line between each corresponding input connection 24 and output connection 26. Carrier tube 12 may also comprise a plurality of input indicia 14 on input end 18 and output indicia 16 on output end 20 that labels each line (e.g. lines 1-4) to aid the user in properly connecting IV lines at respective ends.

Figure 2:
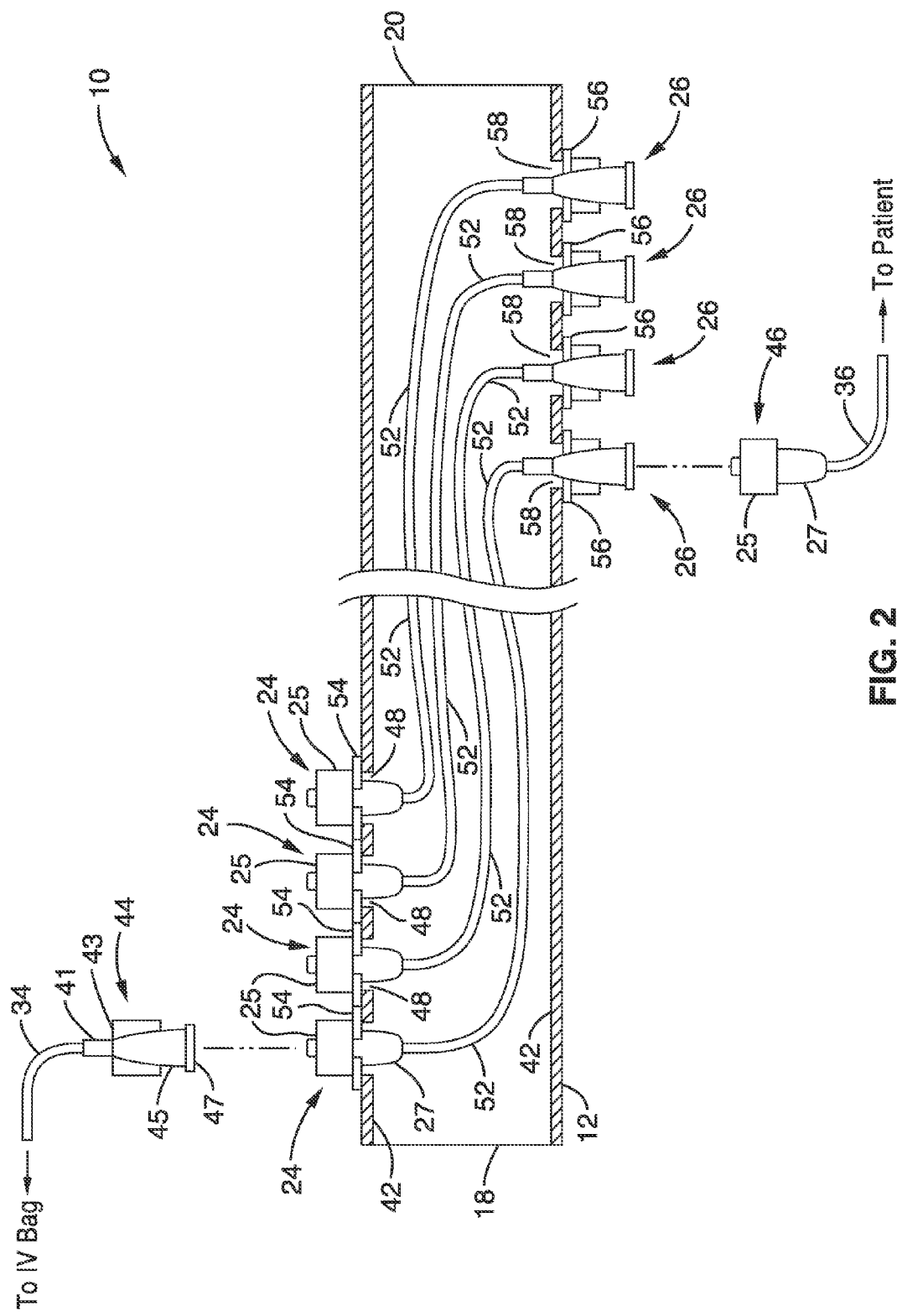
FIG. 2 is a detailed cross-sectional view of the fluid delivery line coupling device of FIG. 1.
Figure 3:
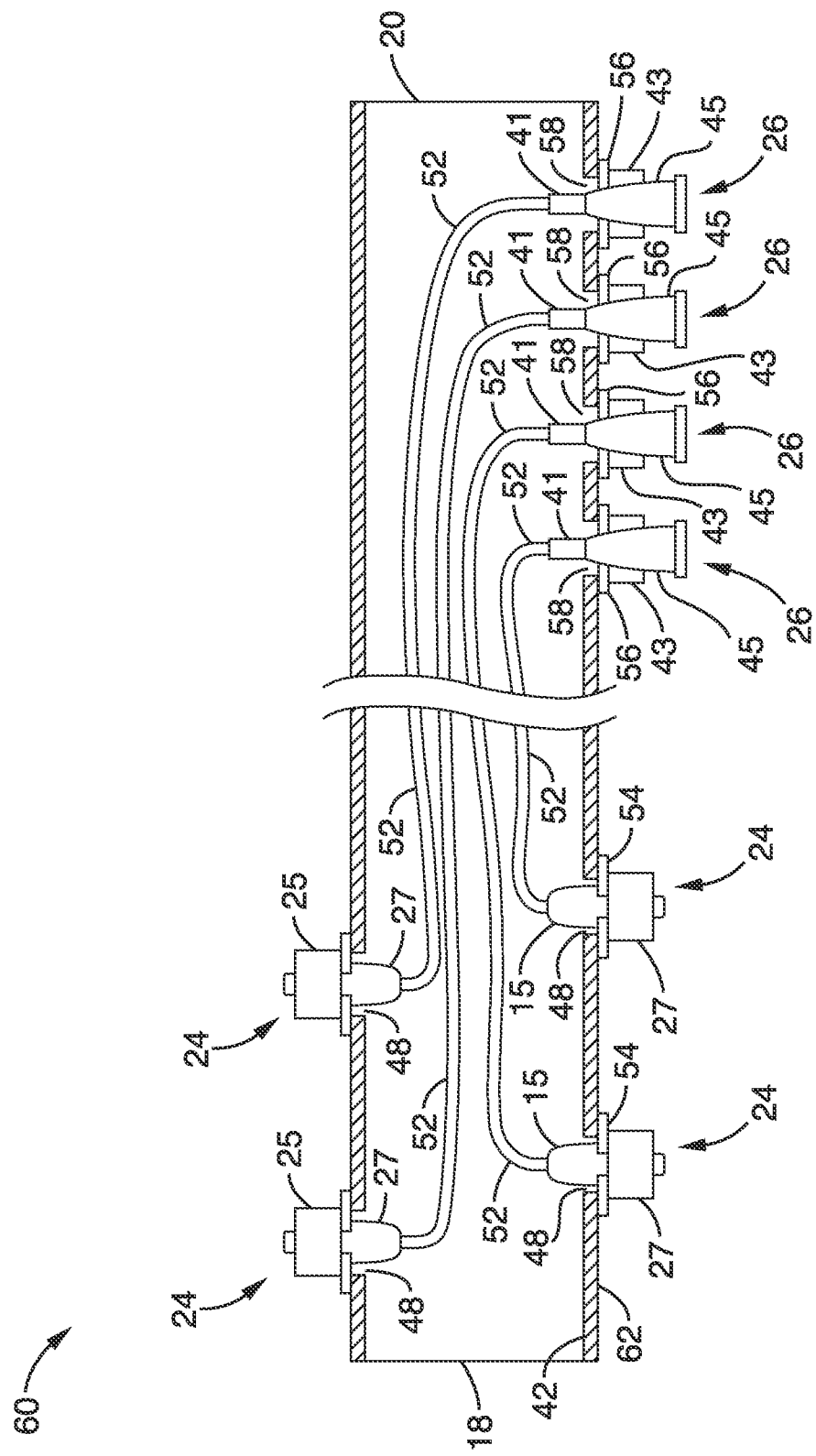
FIG. 3 is a detailed cross-sectional view of a fluid delivery line coupling device having an alternative input line configuration.

FIG. 2 shows a detailed side view of the line coupling device 10, with the carrier tube 12 sectioned for clarity. FIGS. 2 through 4 illustrate a preferred set of embodiments that utilize existing tubing (e.g. IV extension tubing 52 and ventilator tubing 12) to ensure compatibility with various hospital environs and equipment.

Accordingly, the input end 18 of the tube 12 comprises a plurality of input apertures 48 linearly positioned within the wall 42 of the tube 12. The apertures 48 are sized to allow standardized IV extension lines 52, and in particular, are just large enough for the female receiving portion 25 of the input connector 24. Each of the connectors 24 are retained from travelling back into the aperture 48 by corresponding retaining rings 54. The connector 24 and/or retaining ring may optionally be held in place by a biocompatible adhesive or the like.

The input connectors 24 preferably comprise female luer lock couplings that provide a quick release interface with the male luer lock connector 44 of the IV line 34 from IV bags 32. For coupling to the input connector 24, the tabbed end 47 of the male extension 45 is inserted into the receiving portion 25 and rotated (e.g. with manual torque applied at tabs 43) to engage the connector 24 in a sealed and secured fashion. Correspondingly, counter-rotation of the male connector 44 within the receiving portion 25 releases the male connector 44.

The IV extension lines 52 are sized to have a length corresponding to the length of the carrier tube 12 so that the lines 52 extend to the output end 20 of the tube 12. Output end 20 comprises a plurality of output apertures 58 for housing the corresponding output connectors 26.

The apertures 58 are sized to allow standardized IV extension lines 52, and in particular, are just large enough for the tabs 43 of the male output connector 26. Each of the output connectors 26 are retained from travelling back into the aperture 58 by corresponding retaining rings 56. The connector 26 and/or retaining ring 56 may optionally be held in place by a biocompatible adhesive or the like.

The output connectors 26 preferably comprise male luer lock couplings that provide a quick release interface with the female luer lock connector 46 of the IV line 36 that is directed to the patient 38. For coupling to the output connector 26, the receiving portion 25 of the connector 46 is inserted over the tabbed end 47 of the male extension 45 and rotated to engage the connector 26 in a sealed and secured fashion. Correspondingly, counter-rotation of the female connector 46 releases the line 36 from the output connector 26.

It is appreciated that the extension IV lines 52 may comprise, standard bore, mini bore, or micro bore diameters. Correspondingly, the carrier tubing 12 may comprise ventilator tubing or like tubing that is corrugated (not shown).

FIG. 3 is a detailed cross-sectional view of a fluid delivery line coupling device 60 having an alternative input connection configuration. In this configuration, tubing 62 may be configured such that input connectors 24 are positioned in a staggered, opposing configuration. While the output connectors 26 are shown in FIG. 3 in a linear orientation, the output apertures 58 may also be positioned such that the output connectors 26 in the staggered, opposing configuration as illustrated on the input end 18.

FIG. 4 is a side view of a fluid delivery line coupling device 70 having a radial input line configuration. The apertures 48 may be radially positioned within wall 42 of the tube 72 such that the input connectors 24 all point to a common axial center point. Output connectors 26 may be similarly oriented in a radial configuration on opposite end 20.

It is appreciated that the embodiments illustrated in FIGS. 1 through 4 are for illustrative purposes only, and both input connectors 24 and output connectors 26 may comprise any orientation or combination of orientations within tube 12, 62 or 72.

FIG. 5 shows a plan view of a input retainer 54 for coupling the input connectors 24 of IV extension lines 52 to carrier tubing 12, 62, or 72. The input retainer 54 comprises a washer-type ring with a slot 74 having a width W sized according to the diameter of the IV extension lines 52 so that the ring may be placed over the line 52 at the connector 24. The input retainer 54 comprises an outer radius $r_o$ that is larger than the aperture 48 so that the input retainer 54 is restrained from motion back into the aperture. The input retainer 54 also comprises an inner radius $r_i$ sized to be larger than portion 27 of connector 24, while smaller than receiving portion 25 of the connector 24 to retain the receiving portion above the aperture 48.

FIG. 6 is a plan view of an alternative output retainer 56 for coupling the output connectors 26 of the IV extension lines 52 to carrier tubing 12, 62, or 72. The retainer 56 comprises a washer-type ring with a slot 74 having a width W sized according to the diameter of the IV extension lines 52 so that the ring may be placed over the line 52 at the connector 26. The output retainer 56 comprises an outer radius $r_o$ that is larger than the aperture 58 so that the output retainer 56 is restrained from motion back into the aperture 58. The output retainer 56 also comprises an inner radius $r_i$ sized to be larger than portion 41 of connector 26, while smaller than largest diameter of the tapered male extension 45 of the connector 22 to create a snug or interference fit to retain the tab 47 above the aperture 58. The output retainer 56 may also comprise an orthogonal slot 76 to allow the tab 43 to not interfere with the output retainer 56. It is also appreciated that output retainer 56 may also comprise a shape similar to retainer 54 of FIG. 5, with an internal radius $r_i$ sized to be smaller than the length of the tabs 43 of connector 26.

FIG. 7 shows a cross-sectional view of an integrated fluid delivery line coupling device 80 in accordance with the present invention. Coupling device 80 may comprise an injection molded cylindrical section 82 having a plurality of axial apertures 86 that run down the length of the cylinder 82 (ends are capped to retain fluids). Each axial aperture 88 corresponds to a fluid delivery line for a corresponding IV line 34/36. For example, input IV line 34 couples to the tube via a female luer lock extension 84 that is coupled to the corresponding axial aperture 86 via a radial aperture 88. Correspondingly, output IV line 36 couples to the tube 82 via a male luer lock extension (not shown) at end 20 that is coupled to the corresponding axial aperture 86 via a radial aperture.

From the discussion above it will be appreciated that the invention can be embodied in various ways, including the following:

1. A coupling apparatus for fluid delivery to a patient, comprising: a tube having an input end, an output end, and a length therebetween; the input end comprising a plurality of input connections configured to releasably couple to one or more input lines, the one or more input lines being in communication with one or more fluid sources; the output end comprising a plurality of output connections configured to releasably couple to one or more output lines, the one or more output lines being configured to deliver fluid to the patient; and a plurality of lumens disposed within the tube substantially along the length of the tube; wherein each lumen couples one of said plurality of input connectors in fluid communication with a corresponding output connector such that an input line is in fluid communication with a corresponding output line when the input line and output line are connected to a corresponding input connector and output connector.

2. An apparatus as recited in embodiment 1, wherein the plurality of input connections and plurality of output connections are secured to the tube.

3. An apparatus as recited in embodiment 1, wherein the plurality of input connections and plurality of output connections comprise standard IV luer lock connections.

4. An apparatus as recited in embodiment 3, wherein the plurality of lumens comprise standard IV lines.

5. An apparatus as recited in embodiment 3, wherein each lumen and corresponding input connection and output connection comprises a standard IV extension.

6. An apparatus as recited in embodiment 3, further comprising: a plurality of slotted retainers coupled to each of the plurality of input connectors and output connectors; wherein the input connectors and output connectors are secured within a dedicated aperture within the tube, and wherein the slotted retainers retain each of the input connectors and output connectors from retracting within the aperture.

7. An apparatus as recited in embodiment 5, wherein the tube comprises ventilator tubing.

8. An apparatus as recited in embodiment 2, wherein the tube comprises indicia indicating corresponding input connectors and output connectors.

9. A method of delivering fluid from a fluid source to a patient, comprising: providing a tube having an input end, an output end, and a length between the input end and the output end; the input end comprising a plurality of input connections and the output end comprising a plurality of output connections; releasably coupling a first input line from a first fluid source to a first input connection at the input end of the tube; releasably coupling a first output line to a first output connection at the output end of the tube, the output line configured to be coupled to the patient; and delivering fluid from the first fluid source through the first input connection, along the length of the tube, out the first output connection, and into the output line for delivery to the patient.

10. A method as recited in embodiment 9, further comprising: releasably coupling a second input line from a second fluid source to a second input connection at the input end of the tube; releasably coupling a second output line to a second output connection at the output end of the tube, the second output line configured to be coupled to the patient; and delivering fluid from the second fluid source through the second input connection, along the length of the tube, out the second output connection, and into the second output line for delivery to the patient.

11. A method as recited in embodiment 10, wherein fluid is delivered from the first fluid source and second fluid source simultaneously to the patient.

12. A method as recited in embodiment 9: wherein the plurality of input connections and plurality of output connections comprise standard IV luer lock connections; and wherein the first input line and first output lines comprise standard IV lines configured to releasable engage the IV luer lock connections.

13. A method as recited in embodiment 12, wherein the plurality of input connections and plurality of output connections are coupled to each other via dedicated standard IV lines.

14. A method as recited in embodiment 13, wherein each dedicated standard IV line and corresponding input connection and output connection comprises a standard IV extension.

15. A method as recited in embodiment 13, wherein the tube comprises ventilator tubing.

16. A method as recited in embodiment 15, wherein the plurality of input connections and plurality of output connections are secured within apertures in the tube via a plurality of slotted retainers.

17. A method as recited in embodiment 15, wherein the slotted retainers retain each of the input connectors and output connectors from retracting within the aperture.

18. A fluid delivery coupling for fluid delivery to a patient, comprising: a tube having an input end, an output end, and a central channel extending along a length between the input end and the output end; the input end comprising a plurality of input connections configured to releasably couple to one or more input lines, the one or more input lines being in communication with one or more fluid sources; the output end comprising a plurality of output connections configured to releasably couple to one or more output lines, the one or more output lines being configured to deliver fluid to the patient; a plurality of lines disposed within the central channel of the tube and extending substantially along the length of the tube; wherein each line couples one of said plurality of input connectors in fluid communication with a corresponding output connector such that an input line is in fluid communication with a corresponding output line when the input line and output line are connected to a corresponding input connector and output connector.

19. A coupling as recited in embodiment 18, wherein the plurality of input connections and plurality of output connections comprise standard IV luer lock connections; and wherein the plurality of lumens comprise standard IV lines.

20. A coupling as recited in embodiment 18, further comprising: a plurality of slotted retainers coupled to each of the plurality of input connectors and output connectors; wherein the input connectors and output connectors are secured within a dedicated aperture within the tube, and wherein the slotted retainers retain each of the input connectors and output connectors from retracting within the aperture and into the central channel.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A coupling apparatus for fluid delivery to a patient, comprising:
   a compliant tube having an input end, an output end, and a length between the input end and the output end;
   the input end comprising a plurality of input connections configured to releasably couple to one or more input lines, the one or more input lines being in communication with one or more fluid sources;
   the output end comprising a plurality of output connections configured to releasably couple to one or more output lines, the one or more output lines being configured to deliver fluid to the patient;
   a plurality of lumens disposed within the tube substantially along the length of the compliant tube;
   wherein each lumen couples one of said plurality of input connections in fluid communication with a corresponding output connection such that an input line is in fluid communication with a corresponding output line when the input line and output line are connected to a corresponding input connection and output connection;
   wherein the length of the compliant tube is sized to extend along a substantial portion of a distance between the patient and the one or more fluid sources; and
   a plurality of slotted retainers coupled to each of the plurality of input connections and output connections;
   wherein the input connections and output connections are secured within a dedicated aperture within the compliant tube;
   wherein each of the dedicated apertures extends through a wall in the compliant tube; and
   wherein the slotted retainers comprise a disc-shaped structure having an outer diameter configured to retain each of the input connections and output connections from retracting within the aperture.

2. A coupling apparatus as recited in claim 1, wherein the plurality of input connections and plurality of output connections are secured to the tube.

3. A coupling apparatus as recited in claim 2, wherein the tube comprises indicia indicating corresponding input connections and output connections.

4. A coupling apparatus as recited in claim 1, wherein the plurality of input connections and plurality of output connections comprise standard IV luer lock connections.

5. A coupling as recited in claim 4, wherein the plurality of lumens comprise standard IV lines.

6. A coupling apparatus as recited in claim 4, wherein each lumen and corresponding input connection and output connection comprises a standard IV extension.

7. A coupling apparatus as recited in claim 1, wherein the slotted retainers comprise an inner diameter configured to secure to the input connections or output connections.

8. A fluid delivery coupling for fluid delivery to a patient, comprising:
   a compliant tube having an input end, an output end, and a central channel extending along a length between the input end and the output end;
   the input end comprising a plurality of input connections configured to releasably couple to one or more input lines, the one or more input lines being in communication with one or more fluid sources;
   the output end comprising a plurality of output connections configured to releasably couple to one or more output lines, the one or more output lines being configured to deliver fluid to the patient; and
   a plurality of lines disposed within the central channel of the compliant tube and extending substantially along the length of the compliant tube;
   wherein each line couples one of said plurality of input connections in fluid communication with a corresponding output connection such that an input line is in fluid communication with a corresponding output line when the input line and output line are connected to a corresponding input connection and output connection;
   wherein the length of the compliant tube is sized to extend along a substantial portion of a distance between the patient and the one or more fluid sources; and
   a plurality of slotted retainers coupled to each of the plurality of input connections and output connections;
   wherein the input connections and output connections are secured within a dedicated aperture within the compliant tube;
   wherein each of the dedicated apertures extends through a wall in the compliant tube; and
   wherein the slotted retainers comprise a disc-shaped structure having an outer diameter configured to retain each of the input connections and output connections from retracting within the aperture.

9. A coupling as recited in claim 8, wherein the plurality of input connections and plurality of output connections comprise standard IV luer lock connections; and
   wherein the plurality of lumens comprise standard IV lines.

* * * * *